(12) United States Patent
Corbitt, Jr.

(10) Patent No.: US 7,654,266 B2
(45) Date of Patent: Feb. 2, 2010

(54) SURGICAL DRAPING SYSTEM

(76) Inventor: John D. Corbitt, Jr., 142 JFK Dr., Atlantis, FL (US) 33462

( * ) Notice: Subject to any disclaimer, the term of this patent is extended or adjusted under 35 U.S.C. 154(b) by 0 days.

(21) Appl. No.: 10/518,160

(22) PCT Filed: Jun. 10, 2003

(86) PCT No.: PCT/US03/18255

§ 371 (c)(1),
(2), (4) Date: Aug. 15, 2005

(87) PCT Pub. No.: WO03/103525

PCT Pub. Date: Dec. 18, 2003

(65) Prior Publication Data

US 2006/0081261 A1    Apr. 20, 2006

Related U.S. Application Data

(60) Provisional application No. 60/386,758, filed on Jun. 10, 2002, provisional application No. 60/456,552, filed on Mar. 24, 2003.

(51) Int. Cl.
*A61B 19/00* (2006.01)
(52) U.S. Cl. ..................... 128/849; 128/855
(58) Field of Classification Search .......... 128/849–856
See application file for complete search history.

(56) References Cited

U.S. PATENT DOCUMENTS

| | | | |
|---|---|---|---|
| 3,030,957 A | 4/1962 | Melges | |
| 3,410,266 A | 11/1968 | Krzewinski | |
| 3,452,750 A | 7/1969 | Blanford | |
| 3,494,356 A | 2/1970 | Melges | |
| 3,589,365 A | 6/1971 | Sejman | |
| 3,693,618 A * | 9/1972 | Madden | 128/855 |
| 3,911,912 A | 10/1975 | Krebs et al. | |
| 3,930,497 A | 1/1976 | Krebs et al. | |
| 3,942,523 A | 3/1976 | Rudtke | |
| 3,998,221 A | 12/1976 | Collins | |
| 4,119,093 A | 10/1978 | Goodman | |
| 4,334,529 A | 6/1982 | Wirth | |
| 4,349,019 A | 9/1982 | Singer | |
| 4,352,429 A * | 10/1982 | Newman | 206/439 |
| 4,354,486 A * | 10/1982 | Oliver | 128/855 |
| 4,414,968 A | 11/1983 | Amin | |
| 4,471,769 A | 9/1984 | Lockhart | |
| 4,479,492 A * | 10/1984 | Singer | 128/853 |
| 4,520,807 A | 6/1985 | Rotter | |
| 4,570,628 A | 2/1986 | Neal | |
| 4,627,426 A | 12/1986 | Wegener et al. | |
| 4,905,710 A | 3/1990 | Jones | |
| 4,927,073 A * | 5/1990 | Esposito | 229/117.07 |
| 6,244,268 B1 * | 6/2001 | Annett et al. | 128/849 |
| 2002/0147091 A1 * | 10/2002 | Healy et al. | 493/213 |

* cited by examiner

*Primary Examiner*—Michael A. Brown
(74) *Attorney, Agent, or Firm*—Wayne D. Porter, Jr.

(57) ABSTRACT

A surgical draping system (2), separates the sterile surgical field from the unsterile surgical table and isolates the patient so that sterile surgical procedures can be performed without chance of contamination. The components of the surgical draping system are provided folded and in sterile condition inside a sealed bag container. The sealed bag (4), is placed acres an operating table (8), prior to placement of the patient. Once the patient has been positioned on the operating table (8), the bag (4), is opened and the surgical drape (10), is extended. The draping system may include coverings for legs or arms and a top drape. The draping system isolates the operating field in a simple and sterile manner and can be discarded at the termination of the procedure.

16 Claims, 9 Drawing Sheets

SURGICAL DRAPING SYSTEM

BACKGROUND OF THE INVENTION

The present invention relates to a sterile surgical draping system for use during surgical procedures. The system could be used, for example, in surgeries on the perineal area, including but not limited to the buttocks, vaginal area, anal area, and upper thighs, or on the torso and upper extremities, including the head and arms. Many procedures are performed in combination with abdominal surgery or solely surgical intervention of these areas, in which case the area requires a sterile, surgical field. Currently, after the patent is placed on the operating table appropriately for surgery, sheets are pushed under the patent which results in random sterilization and in adequate isolation of the patient from the surgical table. The system provides a method of surgery in which, instead of forcing a sheet underneath a patient's buttocks, shoulder, or head, for example, a drape according to the present invention is place under the patent prior to surgery, and extended to isolate the area of surgical interest from an operating table surface, including operating table extensions, such as leg, shoulder, or head boards.

SUMMARY OF THE INVENTION

The draping system of the present invention isolates the surgical area in a sterile fashion and in a manner that overcomes problems with current methods of draping. The draping system includes a sterile flexible drape, made of cloth, plastic, or paper for example, which is folded, preferably, in an accordion fashion, and placed in a sealed bag. The bag preferably is elongated for placing across an operating table or operating surface. The bag also preferably is perforated so that it can easily be torn open or an edge can separated from the main portion of the bag.

The folded drape, optionally enclosed in a bag, is laid across the operating table, for example, prior to placing the patient on the table. The patient is then placed on the table so that the folded drape lies beneath the patient. In a surgical procedure involving a perineal area, for example, the folded drape would be located near the lower lumbar spine region. After the patient has been positioned properly and prepped, the perforated portion of the bag, which is available for access near the edge of the table, is then opened, preferably simply by pulling by hand, to withdraw the interior accordion sterile drape from the inner portion of the bag. The drape is pulled out so that it covers the table in the area of surgical interest and covers substantially the portion of the operating table down to the floor. Sterile leggings are then placed over the legs of the patient, or in the case of an upper extremity procedure, over one or more of the patient's arm. A top drape with an adhesive strip, for example an abdominal drape with adhesive at the pubic area, also is provided. At the termination of the procedure, the draping system components are discarded. Perforations in the drape are provided to simplify separation and removal of contaminated portions of the drape from those portions of the drape likely to remain in place.

DETAILED DESCRIPTION OS THE PREFERRED EMBODIMENTS

Figure 1:
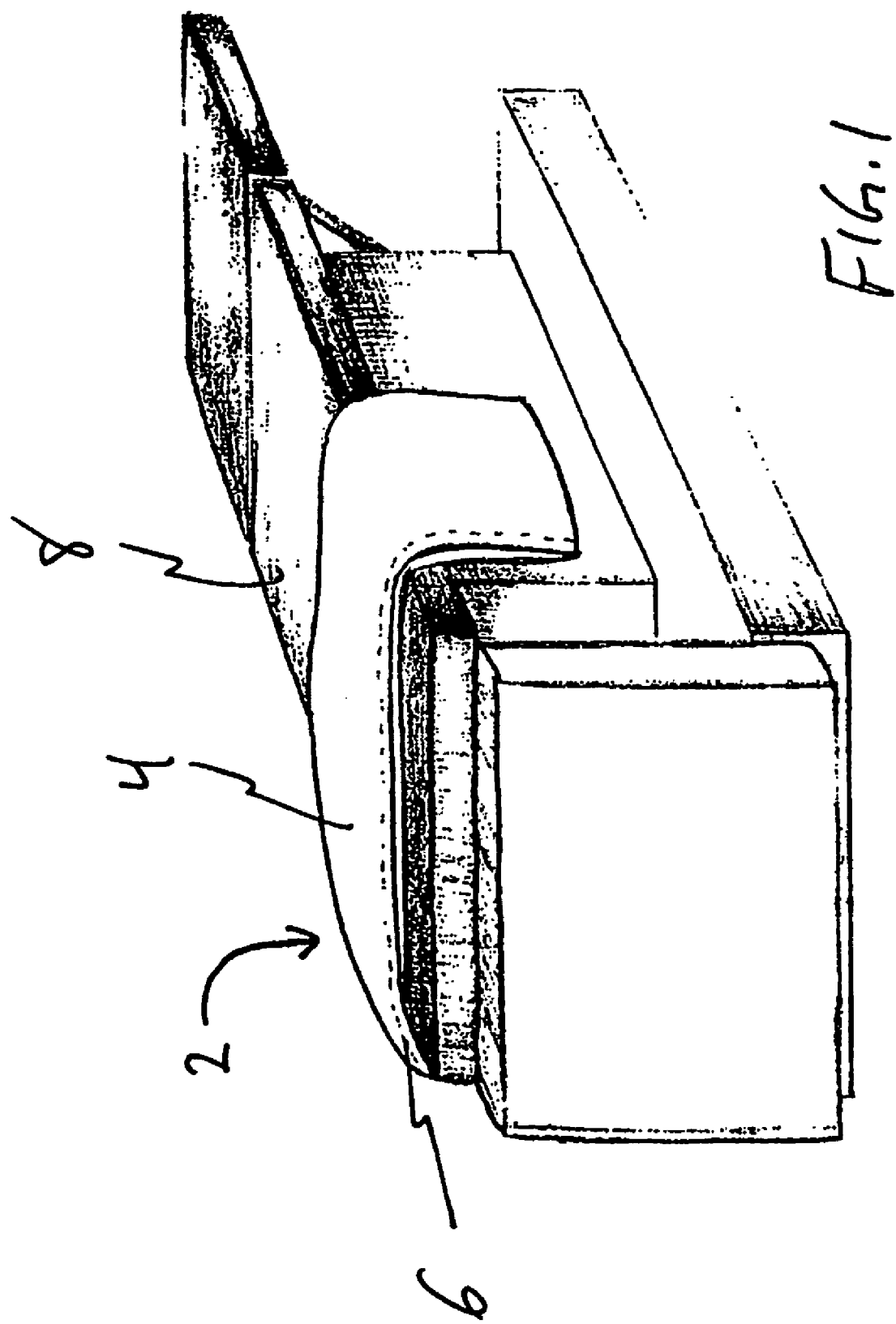
FIG. 1 is a perspective view showing the surgical drape according to an exemplary embodiment of the present invention provided on a surgical table within its original container, with perforations indicated along the leading edge of the sealed package.
Figure 2:
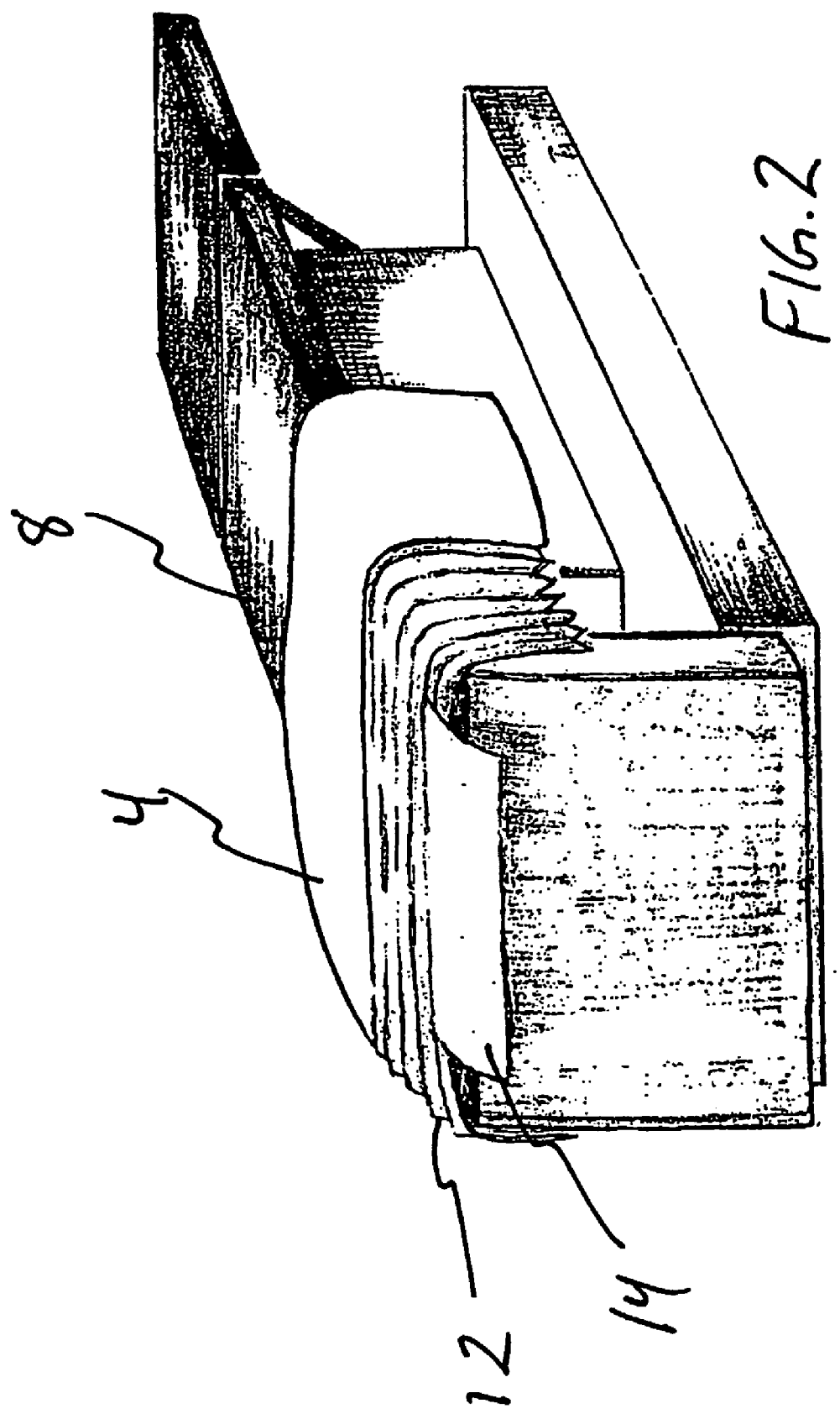
FIG. 2 illustrates the sterile, accordion-folded surgical drape shown in FIG. 1 partially withdrawn from the original container.

Referring to FIG. 1, a surgical drape assembly 2 is shown. The assembly 2 includes a flexible drape 12. The drape 12 is made of flexible material, such as cloth, plastic, paper, or other material capable of being provided or rendered sterile for use in a surgical operating arena. The drape 12 is of sufficient length and width to cover an end of an operating table 8. The drape 12 is provided in a folded condition, preferably, in an accordion fashion to compact the drape 12 along its length. The width of the drape 12 extends beyond the side edges of the operating table 8. The drape 12 optionally is placed in a long, narrow sealed bag 4, which can be placed across the end of the operating table 8 so that it hangs down either side of the table 8. Bag 4 is provided with perforations 6 for ease of tearing open or separation of the edge from the main portion of the bag 4.

Referring to FIGS. 1-7, a method of using the surgical drape assembly 2 is described. A patient 10 (FIGS. 4-7) is not shown in FIGS. 2 and 3 for clarity of illustration. The drape 12, optionally contained within sealed bag 4, initially is laid widthwise across surgical table 8 prior to placing the patient 10 on the table. See FIG. 1. One or more strips of tape or adhesive 24, 26 can be provided on the exterior of the bag 4 or on the drape 12 to aid in securing the bag 4 and/or the drape 12 to the operating table 8. The patient 10 is then placed on the table 8 so that the folded drape 12 lies at the lower lumbar spine region at the edge of the table 8. See FIG. 4. After the patient has been positioned properly and prepped, the perforated portion 6 of the bag 4, which is on the edge of the table 8, or the drape 12 itself, is then pulled to withdraw the sterile drape 12 from the inner portion of the bag 4. An extension or handle 14 is provided on the leading edge of the drape 12 for ease of deployment. See FIGS. 2 and 5.

Figure 3:
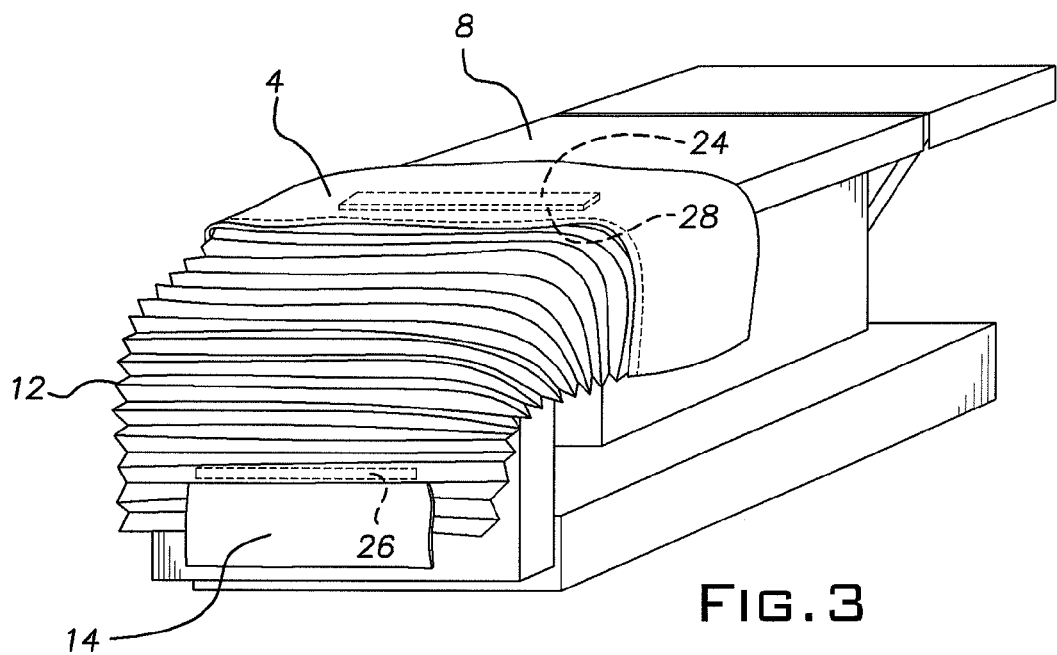
FIG. 3 illustrates an operating room table with the surgical drape of the present invention laying fully extended over the end of the operating table.
Figure 4:
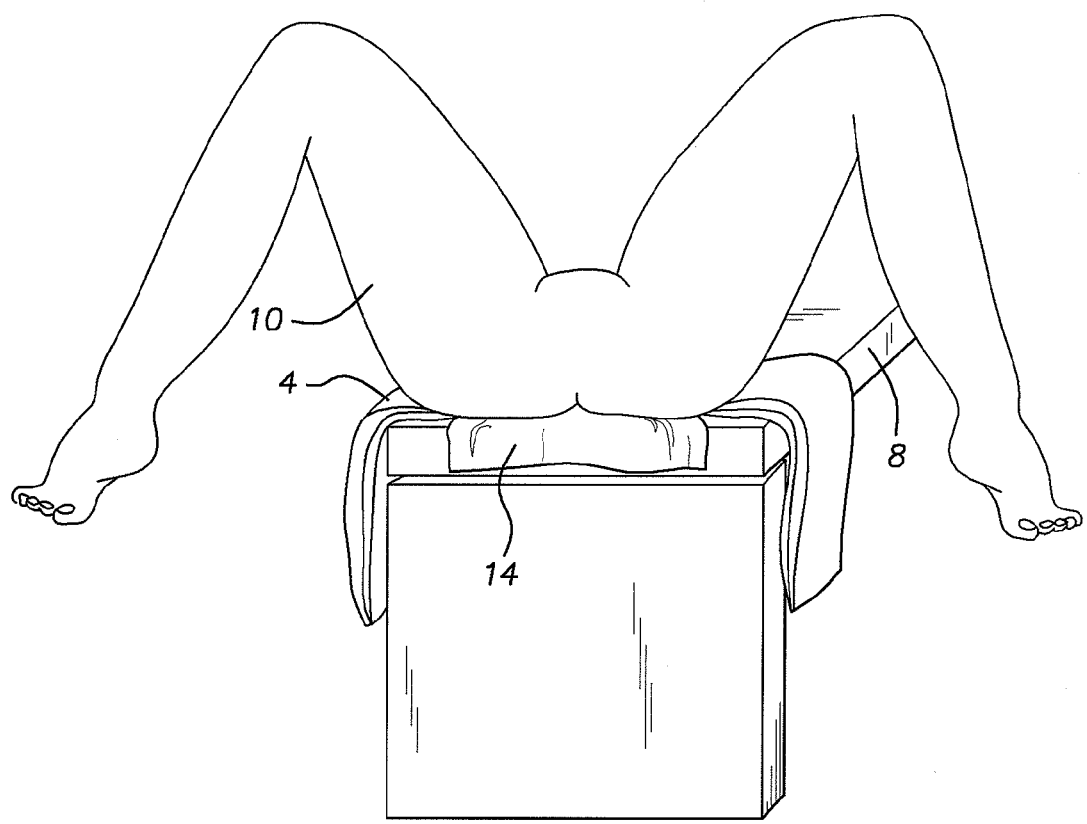
FIG. 4 illustrates a patient placed on top of the folded surgical drape.
Figure 5:
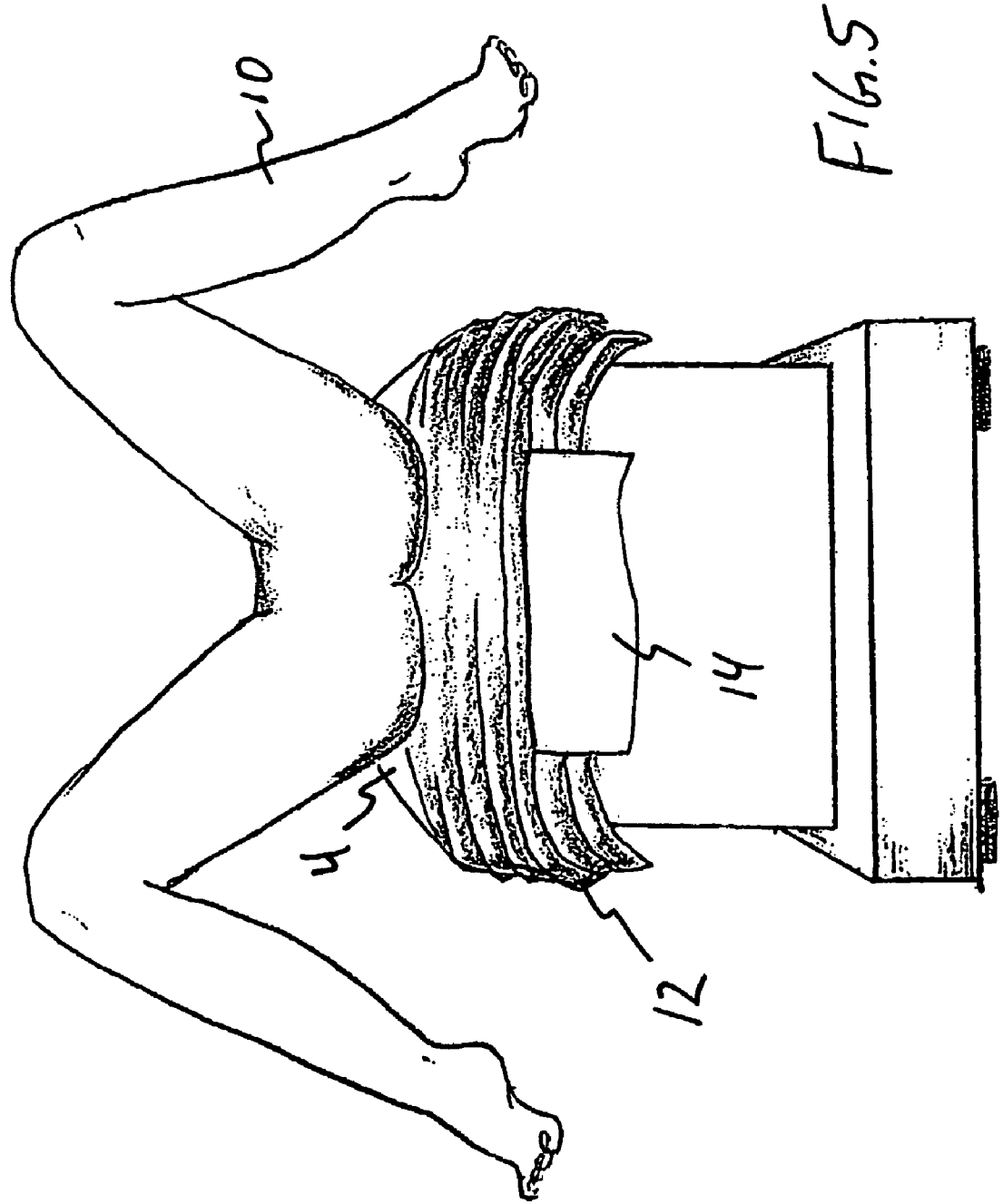
FIG. 5 illustrates the surgical drape being pulled from its container after the perineum of the patient has been prepped.
Figure 6:
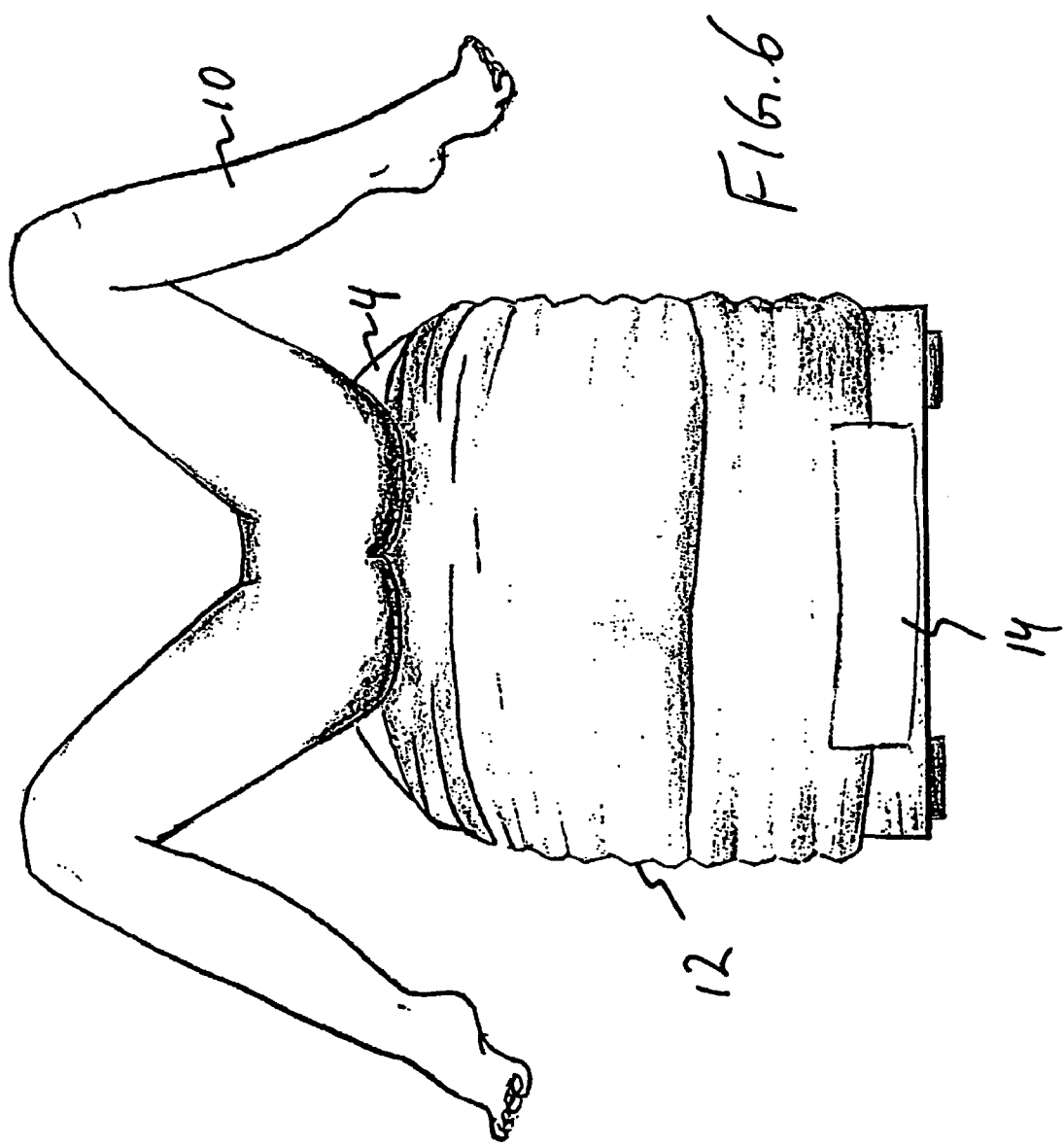
FIG. 6 illustrates the surgical drape in place and fully extended.

Drape 12 is pulled out so that its length covers the table 8 in the area of surgical interest and then covers substantially the entire end of the table 8 down toward the floor, as shown in FIGS. 3 and 6. The drape 12 can provide sterile protection underneath the patient's buttocks, and extend from beneath the patient 10 toward the floor, or the bag 4 itself can provide sterile protection under the patient 10, with the drape 12 providing the remainder of the sterile environment. An adhesive strip 26 can be provided along one or more edges of the drape 12 to secure the drape 12 and prevent slipping. The adhesive strips 24, 26 preferably are protected prior to use by a removable film 28. At least one line of perforations 17 is provided across the drape 12. Perforations 17 allow for tearing away a soiled portion of the drape 12 after completion of the surgical procedure, whereby a lower leg portion of the table 8 can be extended to support the patient's legs on an unsoiled surface. Advantageously, the drape 12 also allows for the optional attachment of a catch basin 19, made of plastic, for example, to the drape 12 under the area of surgery, to catch blood and other contaminants.

Figure 7:
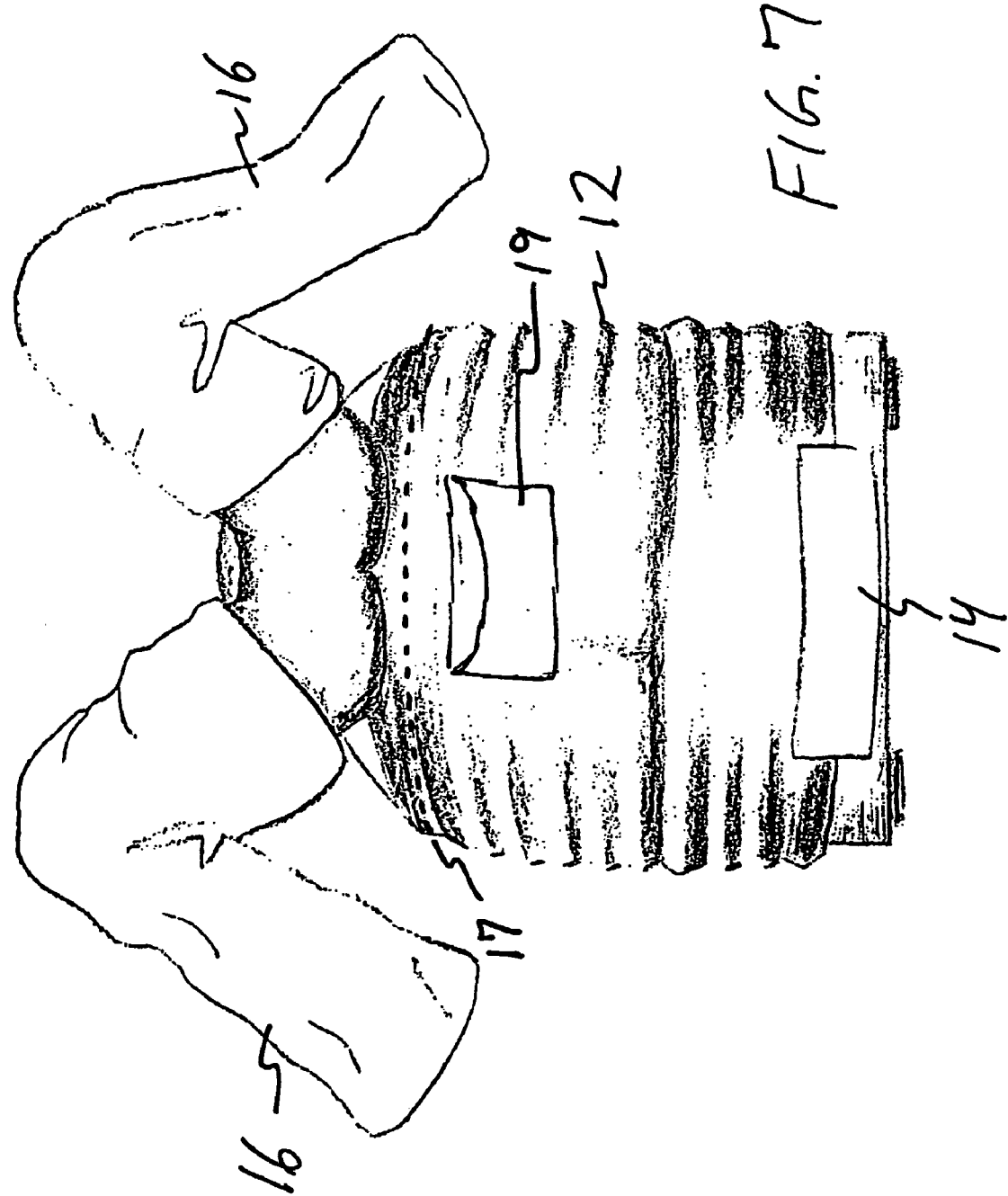
FIG. 7 illustrates the surgical drape in place with leg covers placed over the patient's legs.
Figure 8:
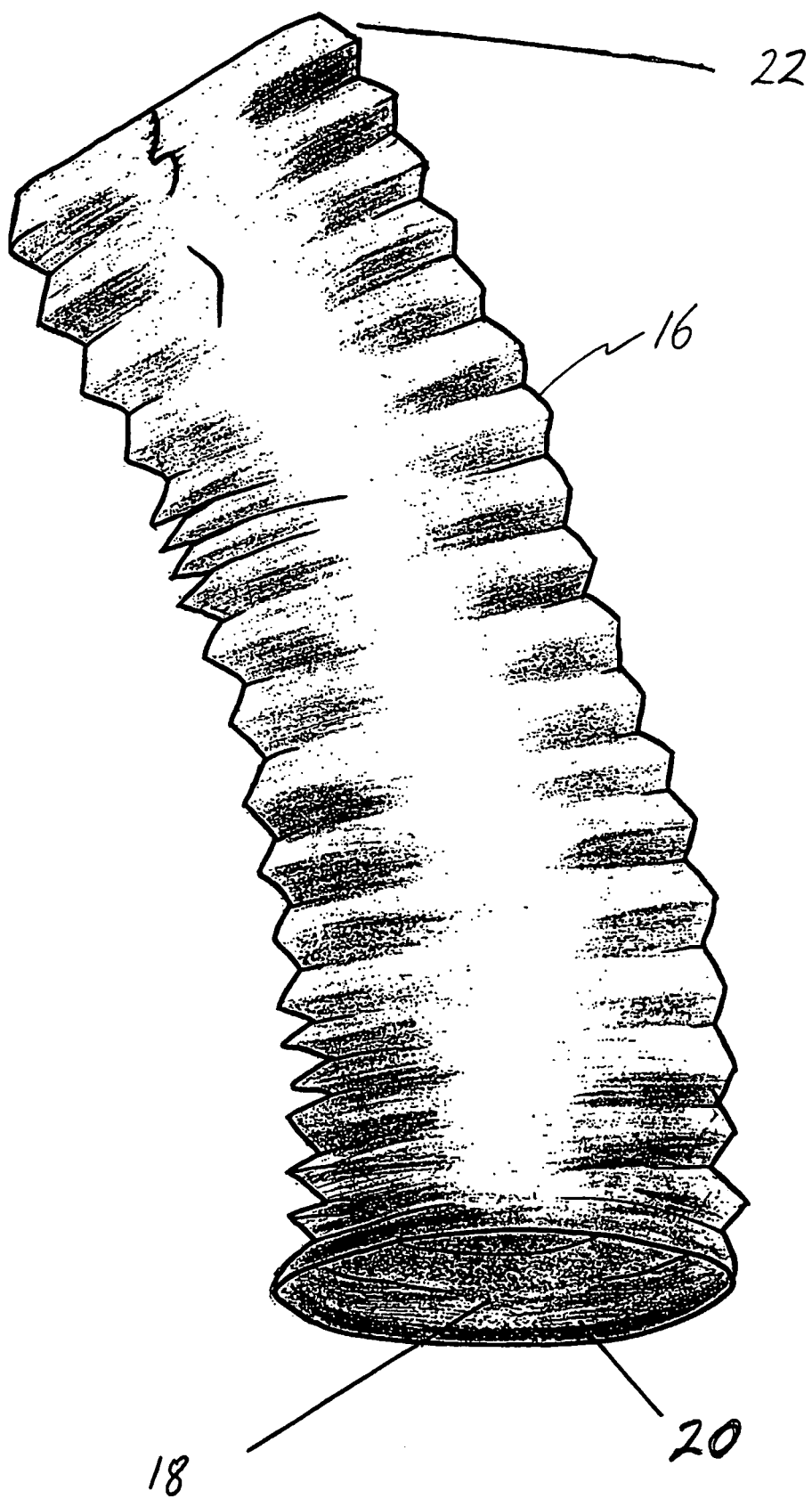
FIG. 8 illustrates a leg or arm cover according to an exemplary embodiment of the present invention.
Figure 9:
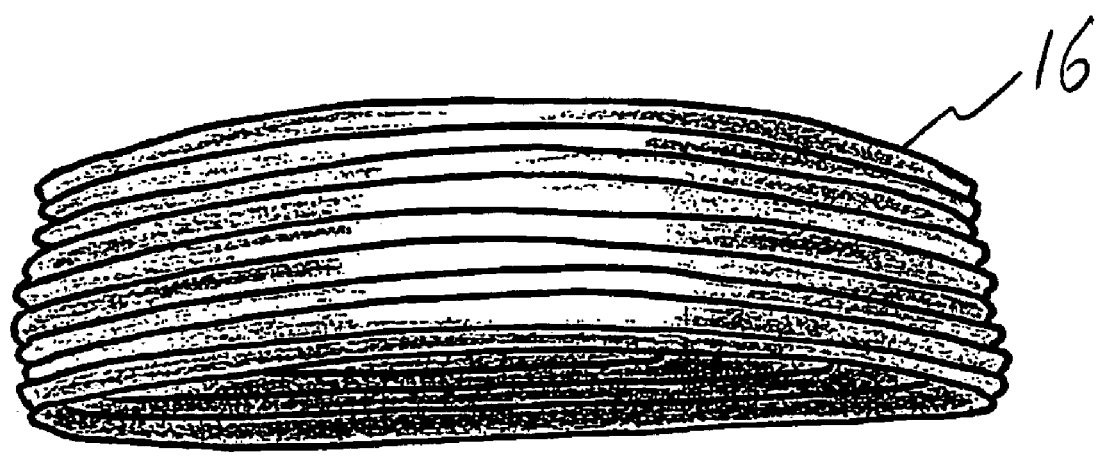
FIG. 9 illustrates the cover of FIG. 8 collapsed for packaging.

Referring to FIG. 7, the draping system of the present invention may include sterile leggings 16. Leggings 16 are placed over the legs of the patient 10, for example, after the patient 10 is placed in stirrups. Leggings 16 can be enclosed with the rest of the draping system along with or in bag 4. An exemplary embodiment of the leg covers 16 according to the present invention is shown in greater detail in FIGS. 8 and 9. The leg covers 16 are shaped like a stocking and have a mouth 18 that is round and open to fit easily over the patient's legs. Advantageously, a stiffener 20 preferably is provided at the mouth 18 of the leg cover 16 to allow the mouth 18 of the leg cover 16 to stay open to facilitate placement of the leg cover 16 over the patient's legs. Prior art leg covers generally are folded, flat, and unnecessarily difficult to slide over a patient's legs. Preferably, the leg covers 16 are at least partially enclosed at a foot end 22, opposite the mouth 18 of the leg cover 16, to cover the patient's feet. The leggings 16 can include perforations for ease of removal after the procedure. FIG. 9 illustrates the leg cover 16 as it is provided prior to surgery, collapsed for packaging. The leg cover 16 can be packaged, for example, in bag 4 with other components of the surgical draping system 2.

Figure 10:
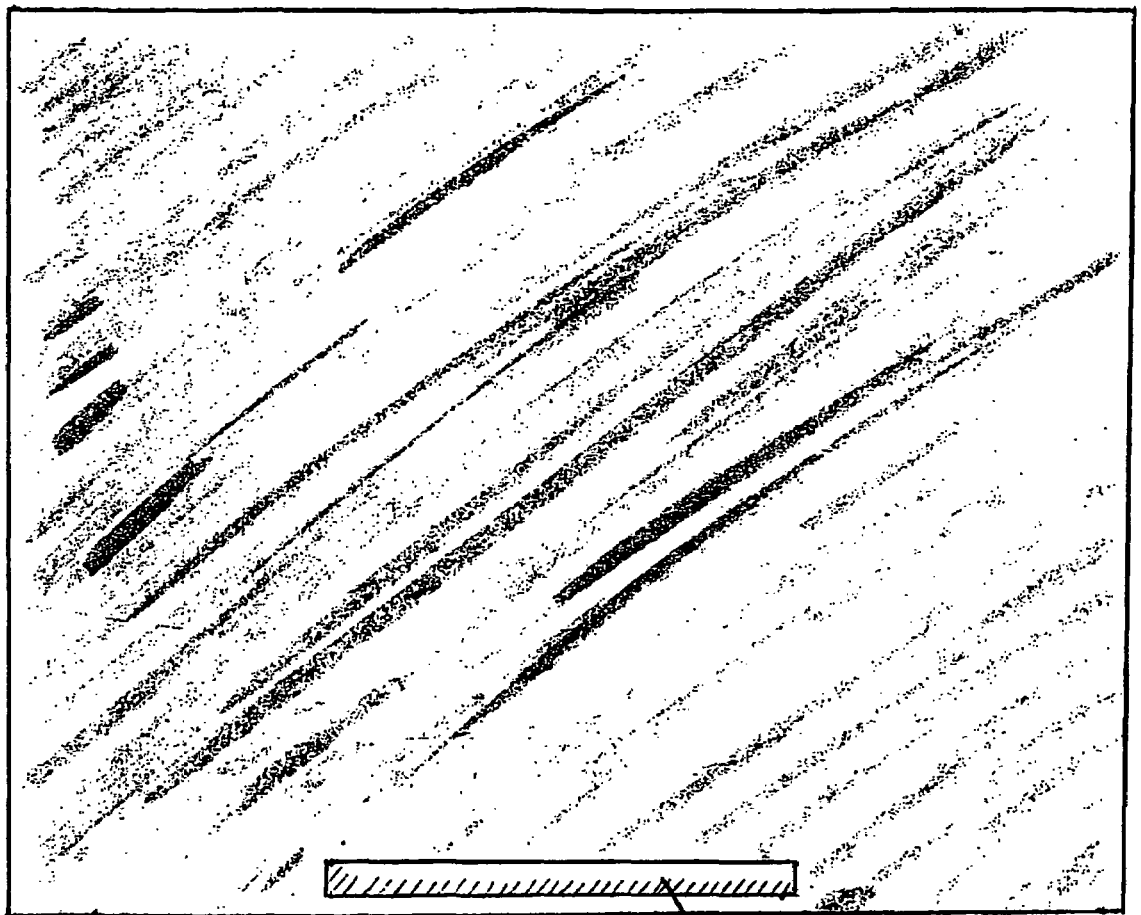
FIG. 10 illustrates an abdominal drape according to an exemplary embodiment of the present invention.

Referring to FIG. 10, an exemplary embodiment of an abdominal or top drape 30 of the draping system is illustrated. Top drape 30 is a flat sheet with adhesive 32 attached on one end so that the adhesive 32 may be placed across the patient's lower pelvis during the draping, prior to surgery. The opposite end, without the adhesive 32, is extended towards the patient's head. The top drape 30 lies over the patient 10 and hangs down off the table 8 on either side. At the termination of the procedure, the drape 12, leg covers 16, top drape 30, and bag 4 are discarded.

While the invention may be susceptible to various modifications and alternative forms, specific embodiments have been shown by way of example in the drawings and have been described in detail herein. However, it should be understood that the invention is not intended to be limited to the particular forms disclosed. For example, although the invention has been described in connection with an exemplary embodiment as a perineal draping system, the system is easily adapted for use in other surgical procedures, such as those involving the arms and the head. In addition, the draping system can include various numbers of components, such as more then one drape, for example, for placement underneath either side of a patient in an abdominal procedure. Thus, the invention is to cover all modifications, equivalents, and alternatives falling within the spirit and scope of the invention as defined by the following appended claims.

What is claimed as new and desired to be protected by Letters Patent of the United States is:

1. A surgical draping system for an operating table having an end and side edges, comprising:
   a bag within which a flexible drape of folded sterilizable material is disposed, the flexible drape adapted to being placed on the operating table prior to a patient being placed on the operating table, the bag and the flexible drape being sufficiently long that they extend beyond the side edges of the operating table;
   a top drape for placement on selected portions of the patient, the top drape including adhesive for attaching the top drape to the patient; and
   wherein, upon opening the bag while the patient is on the operating table, the flexible drape can be extended to cover the end and a portion of the side edges of the operating table.

2. The surgical draping system of claim 1, wherein the flexible drape is folded with accordion folds.

3. The surgical draping system of claim 1, wherein the flexible drape has a leading edge, and further comprising a handle connected to, and extending from, the leading edge.

4. The surgical draping system of claim 1, further comprising adhesive on the flexible drape for securing the flexible drape to the operating table.

5. The surgical draping system of claim 1, further comprising a bag having a perforated portion, the flexible drape being disposed within the bag, and at least a portion of the flexible drape being removable from the bag upon opening the perforated portion.

6. The surgical draping system of claim 5, further comprising adhesive on the bag for securing the bag to the operating table.

7. The surgical draping system of claim 1, further comprising at least one legging for placement over an extremity of the patient.

8. The surgical draping system of claim 1, wherein the folded flexible surgical drape is in a sterilized condition while in the bag and the bag has not been opened.

9. A method of isolating a patient from an operating table in surgical procedures using a surgical draping system, the method comprising:
   providing a bag;
   providing a flexible surgical drape;
   folding the flexible surgical drape;
   placing the folded flexible surgical drape in the bag;
   placing the bag and the folded flexible surgical drape on the operating table;
   placing the patient on the bag and the folded flexible surgical drape;
   opening the bag; and
   unfolding the folded flexible surgical drape to isolate the patient from the operating table.

10. The method of claim 9, further comprising the steps of:
    providing adhesive for the flexible surgical drape; and
    attaching the unfolded flexible surgical drape to the operating table by use of the adhesive.

11. The method of claim 9, further comprising the steps of:
    providing adhesive for the bag; and
    attaching the bag to the operating table by use of the adhesive.

12. The method of claim 9, further comprising the steps of:
    providing at least one legging; and
    covering an extremity of the patient with the legging.

13. The method of claim 9, further comprising the steps of:
    providing a top drape for placement on selected portions of the patient;
    providing adhesive for the top drape; and
    attaching the top drape to the patient by use of the adhesive.

14. The method of claim 9, further comprising the steps of:
    sterilizing the flexible surgical drape prior to the step of placing the folded flexible surgical drape in the bag; and
    sealing the bag after the sterilized folded flexible surgical drape has been placed therein.

15. The method of claim 9, wherein the operating table has side edges, and the bag and the unfolded flexible surgical drape extend beyond the side edges.

16. The method of claim 15, wherein the operating table also has an end, and the step of unfolding the folded flexible surgical drape causes the end and the side edges of the operating table to be covered.

* * * * *